(12) United States Patent
Abunahla et al.

(10) Patent No.: US 12,247,942 B2
(45) Date of Patent: Mar. 11, 2025

(54) GLUCOSE SENSING DEVICE

(71) Applicant: Khalifa University of Science and Technology, Abu Dhabi (AE)

(72) Inventors: Heba Abunahla, Abu Dhabi (AE);
Baker Mohammad, Abu Dhabi (AE);
Anas Alazzam, Abu Dhabi (AE);
Maguy Abi Jaoude, Abu Dhabi (AE);
Mahmoud Al-Qutayri, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 855 days.

(21) Appl. No.: 17/058,485

(22) PCT Filed: Jun. 3, 2019

(86) PCT No.: PCT/IB2019/054594
§ 371 (c)(1),
(2) Date: Nov. 24, 2020

(87) PCT Pub. No.: WO2019/234596
PCT Pub. Date: Dec. 12, 2019

(65) Prior Publication Data
US 2021/0116410 A1 Apr. 22, 2021

Related U.S. Application Data

(60) Provisional application No. 62/681,294, filed on Jun. 6, 2018.

(51) Int. Cl.
*G01N 27/327* (2006.01)
*G01N 33/49* (2006.01)
*G01N 33/66* (2006.01)

(52) U.S. Cl.
CPC ......... *G01N 27/3277* (2013.01); *G01N 33/49* (2013.01); *G01N 33/66* (2013.01)

(58) Field of Classification Search
CPC .... G01N 27/3277; G01N 33/49; G01N 33/66; G01N 33/5438; A61B 5/14532
See application file for complete search history.

(56) References Cited

U.S. PATENT DOCUMENTS

2004/0248282 A1* 12/2004 Sobha M. .......... G01N 27/3278
435/287.2
2007/0208243 A1 9/2007 Gabriel et al.
(Continued)

FOREIGN PATENT DOCUMENTS

KR 20090081762 A * 7/2009
KR 20110138753 A * 12/2011
(Continued)

OTHER PUBLICATIONS

Jang, English translation of KR20110138753A, 2011 (Year: 2011).*
(Continued)

*Primary Examiner* — Luan V Van
*Assistant Examiner* — Shizhi Qian
(74) *Attorney, Agent, or Firm* — Kilpatrick Townsend & Stockton LLP

(57) ABSTRACT

A glucose sensor includes an insulating metal oxide layer and at least one pair of metallic electrodes arranged on the insulating metal oxide layer and separated by a gap containing the metal oxide layer. In operation, a probe including a voltage supply and current sensor can provide a voltage difference across the first and second metallic electrodes while a sample is present across the gap between the electrodes. A measured current between the first and second metallic electrodes when the voltage difference is provided can be correlated to a glucose level of the sample.

18 Claims, 5 Drawing Sheets

(56) References Cited

U.S. PATENT DOCUMENTS

| | | | |
|---|---|---|---|
| 2008/0093226 | A1 | 4/2008 | Briman et al. |
| 2011/0021894 | A1 | 1/2011 | Mohanty et al. |
| 2014/0054171 | A1 | 2/2014 | Feldman et al. |
| 2014/0061044 | A1 | 3/2014 | Thekkedath et al. |
| 2014/0332407 | A1 | 11/2014 | Mai et al. |
| 2015/0168336 | A1* | 6/2015 | Diguet ............... G01N 27/3272 204/400 |
| 2017/0188914 | A1* | 7/2017 | Dutta ................... A61B 5/1455 |
| 2018/0059051 | A1* | 3/2018 | Yang ................... G01N 33/552 |
| 2019/0137437 | A1* | 5/2019 | Raveendran ........... G01N 27/48 |

FOREIGN PATENT DOCUMENTS

| | | | |
|---|---|---|---|
| KR | 20120091792 | A | 8/2012 |
| KR | 20130107915 | A | 10/2013 |
| KR | 101436162 | B1 | 9/2014 |
| KR | 20140132869 | A | 11/2014 |
| WO | WO1990012314 | A1 * | 10/1990 |
| WO | 03042396 | | 5/2003 |
| WO | 2009046161 | | 4/2009 |

OTHER PUBLICATIONS

Wang et al., Channel-width dependent enhancement in nanoscale field effect transistor, https://arxiv.org/abs/0802.2140, 2008 (Year: 2008).*
Chen et al., Quasi-two-dimensional metal oxide semiconductors based ultrasensitive potentiometric biosensors, ACS Nano, Nov. 2017, 4710-4718 (Year: 2017).*
Ahmad et al., Fabrication of a non-enzymatic glucose sensor field-effect transistor based on vertically-oriented ZnO nanorods modified with Fe2O3, Electrochemistry Communication, 2017, 77, 107-111 (Year: 2017).*
Schneider et al., A printed and flexible field effect transistor device with nanoscale zinc oxide as active semiconductor material, Advanced Materials, 2008, 20, 3383-3387 (Year: 2008).*
DiabetesChart, Covert glucose (mg/dl) to Glucose (mmol/L), available from https://www.diabeteschart.org/mgmmol.html, Jan. 27, 2010 (Year: 2010).*
Application No. EP19816155.6 , Extended European Search Report, Mailed On Feb. 21, 2022, 9 pages.
Sideeq et al., "Nozzle-Jet Printed Flexible Field-Effect Transistor Biosensor For High Performance Glucose Detection", Journal Of Colloid And Interface Science, vol. 506, Nov. 1, 2017, pp. 188-196.
Zhenzhen et al., "Rational Design Of Binder-Free Noble Metal/Metal Oxide Arrays With Nanocauliflower Structure For Wide Linear Range Nonenzymatic Glucose Detection", Scientific Reports, vol. 5, No. 1, Sep. 1, 2015, pp. 1-10.
M. Ahmad, C. Pan, Z. Luo and J. Zhu, J. Phys. Chem. C, 2010, 114, 9308.
X. Li, Y. Zhou, Z. Zheng, X. Yue, Z. Dai, S. Liu and Z. Tang, Langmuir, 2009, 25, 6580.
E. S. Forzani, H. Zhang, L. A. Nagahara, I. Amlani, R. Tsui and N. Tao, Nano Lett., Apr. 2004, 1785.
R. Ahmad, M. Vaseem, N. Tripathy and Y.-B. Hahn, Anal. Chem., 2013, 85, 10448.
A. Pandya, P. G. Sutariya and S. K. Menon, Analyst, 2013, 138, 2483.
H. Pang, Q. Lu, J. Wang, Y. Li and F. Gao, Chem. Commun., 2010, 46, 2010.
J. Huang, Z. Dong, Y. Li, J. Li, J. Wang, H. Yang, S. Li, S. Guo, J. Jin and R. Li, Sens. Actuators, B, 2013, 182, 618.
T.-M. Cheng, T.-K. Huang, H.-K. Lin, S.-P. Tung, Y.-L. Chen, C.-Y. Lee and H.-T. Chiu, ACS Appl. Mater. Interfaces, Feb. 2010, 2773.
C. Guo, Y. Wang, Y. Zhao and C. Xu, Anal. Methods, May 2013, 1644.
J. Wang, D. F. Thomas and A. Chen, Anal. Chem., 2008, 80, 997.
X.-C. Dong, H. Xu, X.-W. Wang, Y.-X. Huang, M. B. Chan-Park, H. Zhang, L.-H. Wang, W. Huang and P. Chen, ACS Nano, Jun. 2012, 3206.
B. Fang, A. Gu, G. Wang, W. Wang, Y. Feng, C. Zhang and X. Zhang, ACS Appl. Mater. Interfaces, Jan. 2009, 2829.
Ahmad, R., Tripathy, N., Ahn, M. S., Bhat, K. S., Mahmoudi, T., Wang, Y., & Hahn, Y. B., Scientific Reports, 2017, 7(1), 5715.
S. Xu, H. Li, L. Wang, Q. Yue, S. Sun and J. Liu, CrystEngComm, 2014, 16, 9075.
R. Khan, R. Ahmad, P. Rai, L.-W. Jang, J.-H. Yun, Y.-T. Yu, Y.-B. Hahn and I.-H. Leea, Sens. Actuators, B, 2014, 203, 471.
S. Liu, B. Yu and T. Zhang, Electrochim. Acta, 2013, 102, 104.
J. Luo, S. Jiang, H. Zhang, J. Jiang and X. Liu, Anal. Chim. Acta, 2012, 709, 47.
X. Li, J. Yao, F. Liu, H. He, M. Zhou, N. Mao, P. Xiao and Y. Zhang, Sens. Actuators, B, 2013, 181, 501.
A. Sun, J. Zhenga and Q. Sheng, Electrochim. Acta, 2012, 65, 64.
J. Zhao, L. Wei, C. Peng, Y. Su, Z. Yang, L. Zhang, H. Wei and Y. Zhang, Biosens. Bioelectron., 2013, 47, 86.
A. A. Saei, J. E. N. Dolatabadi, P. Najafi-Marandi, A. Abhari and M. de la Guardia, TrAC Trends Anal. Chem., 2013, 42, 216.
Ahmad, R., Tripathy, N., Hahn, Y. B., Umar, A., Ibrahim, A. A., & Kim, S. H, Dalton Transactions, 2015, 44(28), 12488-12492.
Application No. PCT/IB2019/054594 , International Search Report and Written Opinion, Mailed On Oct. 21, 2019, 12 pages.
Ahmad et al., "Fabrication of a Non-enzymatic Glucose Sensor Field-effect Transistor Based on Vertically-oriented ZnO Nanorods Modified With Fe2O3", Electrochemistry Communications, vol. 77, Apr. 2017, pp. 107-111.
Bell et al., "Flexible Electronics-compatible Nonenzymatic Glucose Sensing via Transparent CuO Nanowire Networks on PET Films", Nanotechnology, vol. 28, May 25, 2017, pp. 1-11.
Cella, et al., "Single-Walled Carbon Nanotube-Based Chemiresistive Affinity Biosensors for Small Molecules: Ultrasensitive Glucose Detection", J.AM.Chem. Soc. vol. 132, 2010, pp. 5024-5026.
EP19816155.6 , "Office Action", Mar. 1, 2024, 5 pages.

* cited by examiner

GLUCOSE SENSING DEVICE

BACKGROUND

Glucose is naturally present in the blood of humans and other animals, and the concentration of glucose in the blood is interchangeably referred to as the blood sugar or blood glucose level or concentration. Glucose is a simple sugar and is a primary metabolite in human physiology, with several grams of blood glucose often present at any given time throughout an adult human body. However, the glucose level is tightly regulated, as it is both critical for normal functioning and toxic when present in excess for long periods of time. Irregularities in glucose level are present in several medical conditions. For example, diabetes typically presents as hyperglycemia, or excess blood glucose, often caused by resistance to or low levels of insulin.

There are various methods of testing and measuring blood glucose levels, most of which are enzyme-based and expensive. Regular glucose monitoring allows both patients and doctors to monitor patient blood glucose levels, in order to inform diet and medication requirements. Some existing devices include chemical test strips, blood glucose meters, or implantable glucose monitors that interact with patient blood to provide a blood glucose reading. However, improved devices that save on costs and efficiency are needed.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In at least one embodiment, a glucose sensor includes an insulating metal oxide layer, at least one pair of first and second metallic electrodes arranged on or within the insulating metal oxide layer and separated by a gap, and a probe configured to supply voltage and measure current across the first and second metallic electrodes when a sample is applied to the gap and electrodes. The oxide layer can be between the metallic electrodes, or even partially over the electrodes. In some embodiments, the metallic electrodes are partially, or even fully embedded in the oxide layer. The sensor can further include electrically inert substrate supporting the insulating metal oxide layer. In some embodiments, multiple pairs, and potentially many pairs, of the first and second metallic electrodes can be arranged in a grid on the insulating metal oxide layer. Suitable electrode materials can include but are not limited to Pt electrodes; and the insulating metal oxide layer can be composed of but is not limited to CuO. In some embodiments, the glucose sensor is capable of differentiating dissolved glucose levels in a liquid sample in the range of 40 mg/dl to at least 180 mg/dl when the liquid sample is at a pH of 7.

In accordance with at least one other embodiment, a method of detecting blood glucose includes placing a blood sample on a gap between the electrodes of a glucose sensor as described above, subjecting the sensor to a voltage difference applied to the first and second metallic electrodes, and measuring a current through the sensor. The glucose level of the blood sample can be determined based on the measured current. In accordance with various embodiments, the methods described herein can be performed without diluting the blood sample, where the blood sample has a pH of approximately 7, and at an applied voltage on the order of about 1V across the sensor. In some embodiments, averaged glucose sensing results can be obtained by placing the blood sample across multiple sensors arranged in a grid on the metal oxide layer, each pair separated by a respective gap, and subjecting each sensor to a respective voltage difference. Multiple currents through the respective sensors can be measured and used to determining the blood glucose level of the blood sample based on, e.g., an average or other suitable statistical operation.

For a more complete understanding of the nature and advantages of the present invention, reference should be made to the ensuing detailed description and accompanying drawings.

BRIEF DESCRIPTION OF THE DRAWINGS

Various embodiments in accordance with the present disclosure will be described with reference to the drawings, in which.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments described in the present disclosure relate to a blood glucose sensor formed as a metal-insulator-metal (MIM) device. The MIM device uses a simple and inexpensive process to produce a sensor that can respond to different glucose concentration by changing the electrical resistivity and therefore a current applied across the device. In some embodiments, the sensor demonstrates sensitivity between (40-180) mg/dl of concentration.

Previous glucose sensing devices have been largely enzyme-based. Such devices have several inherent disadvantages such as high cost and unsatisfactory reproducibility. To overcome such issues, recent efforts have been made to target non-enzymatic sensors such as sensors employing metal oxides (e.g., NiO, $Cu_2O$, CuO, $TiO_2$, ZnO, $SnO_2$, $MnO_2$, $Co_3O_4$, etc.) that have the ability to interact with glucose in the absence of enzymes. Among the used materials, CuO has shown excellent properties to be used in glucose sensing; such as low production cost, high stability and its appropriate redox potential.

However, previous CuO-based sensors require a medium at high pH, e.g. a pH of 13 or greater. Thus, using such devices requires diluting and increasing the pH of a blood sample prior to use. In contrast, sensors disclosed herein can sense blood glucose in a sample at a neutral pH (i.e., pH=7), which allows the device to use samples of blood directly without an intermediate processing step.

Figure 1:
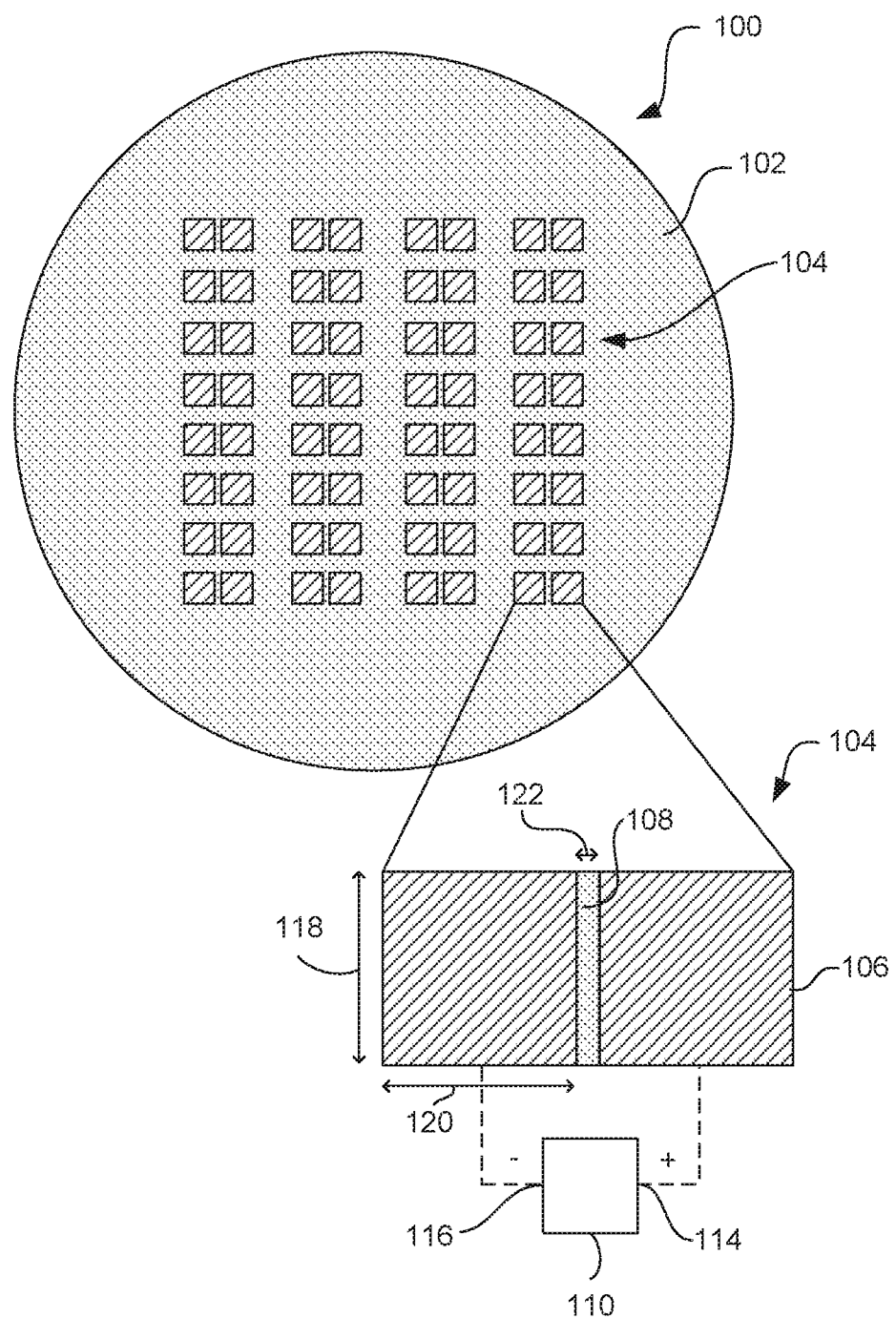
FIG. 1 is a schematic top view of a glucose sensing device having a grid of multiple sensing elements, in accordance with at least one embodiment of the present disclosure.

FIG. 1 shows a testing device 100 that includes a surface 102 formed of an insulator, e.g. CuO, containing a grid of sensors 104. Each sensor 104 is composed of a pair of metal electrodes 106 separated by a narrow gap 108, which is composed of the insulating surface. The specific dimensions of the sensors 104 can vary depending on the application, but in one embodiment, the metal electrodes 106 have a length and width 118, 120 of about 3 mm, and the gap 108 has a width 122 of about 50 μm. In operation, each sensor 104 of the device 100 can be used by placing a sample over the gap 108 so that it contacts both electrodes 106, and applying a voltage across the gap from a positive lead 114 and negative lead 116 of a test power source 110. In the examples described below, a 1V test voltage was applied. Although samples can be applied individually to each sensor 104, the entire device 100 may also be subjected to a large sample, such that multiple sensors 104 can be recruited to provide duplicate readings of the same sample.

Figure 2:
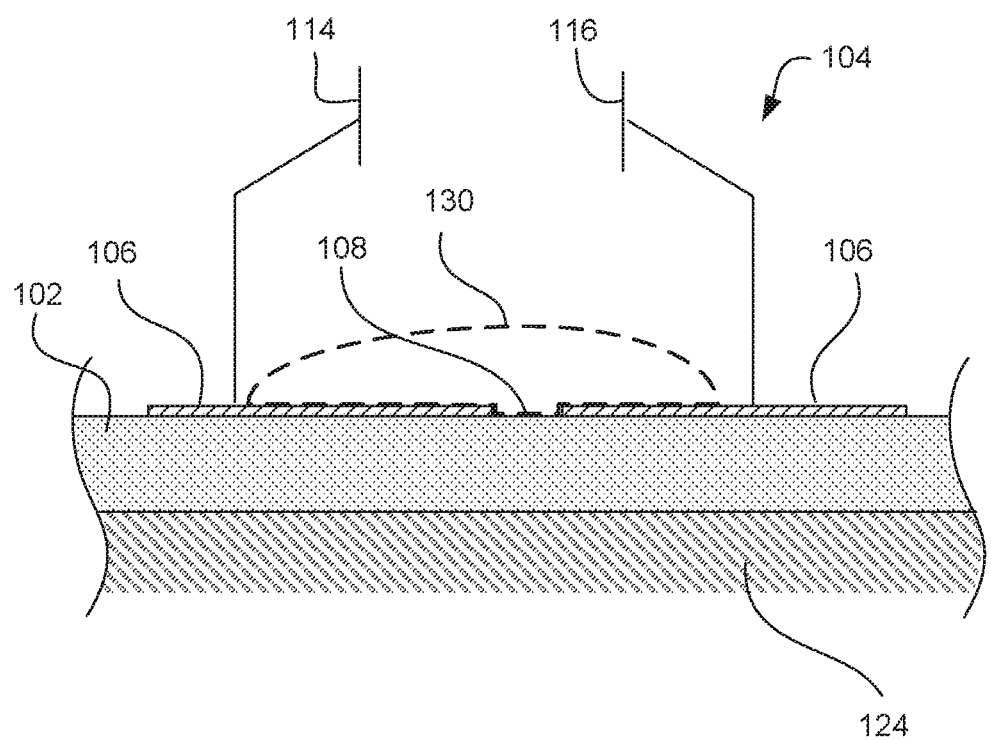
FIG. 2 is a side section schematic of the sensing element of the sensing device of FIG. 1.

FIG. 2 shows a portion of the testing device 100 of FIG. 1, focusing on a single sensor 104 in a side cross-section view. The sensor 104 includes two metal electrodes 106 separated by a gap 108 formed of the insulating surface 102. The insulating surface 102 extends below the metal electrodes 106, and rests on a substrate layer 124, which can be any suitable inert structural layer, such as but not limited to glass.

In use, the sensor 104 is subjected to a liquid sample of blood 130 which is positioned on the sensor bridging the metal electrodes 106 and covering the insulator 102 along the gap 108. In some use cases, the sample can be placed directly on the gap 108. In alternative use cases, the sample can be placed across a larger area of the device 100 so that the sample covers several of the sensors 104. The blood glucose level of the sample 130 can be measured by providing a voltage across the pair of metal electrodes 106, e.g. by leads 114 and 116, and measuring a current corresponding to the applied voltage. The sensors 104 disclosed herein can advantageously be used for sensing blood glucose at a pH at or near 7, without an intervening step of changing the blood sample pH. In some embodiments, blood glucose may be measured in a blood sample directly. In some other embodiments, blood glucose may be measured in a blood sample after a separation step to remove contaminants or other ions in the blood sample.

The thicknesses of the metal electrodes 106 and insulating layer 102 can vary with the specific use case, however, in at least one embodiment, the metal electrodes 106 are on the order of 10-30 nm thick, preferably 20-22 nm thick, and the insulating layer 102 is on the order of 10-30 nm thick, and preferably 26-28 nm thick. In some embodiments, the metal electrodes 106 can rest on top of the insulating layer 102, or can be positioned embedded in the insulating layer. In at least one embodiment, the metal electrodes 106 are composed of Pt and the insulating layer is an insulating metal oxide such as, but not limited to, CuO. In some alternative embodiments, the insulating layer is another metal oxide layer, such as but not limited to NiO, $Cu_2O$, CuO, $TiO_2$, ZnO, $SnO_2$, $MnO_2$, or $Co_3O_4$.

Figure 3:
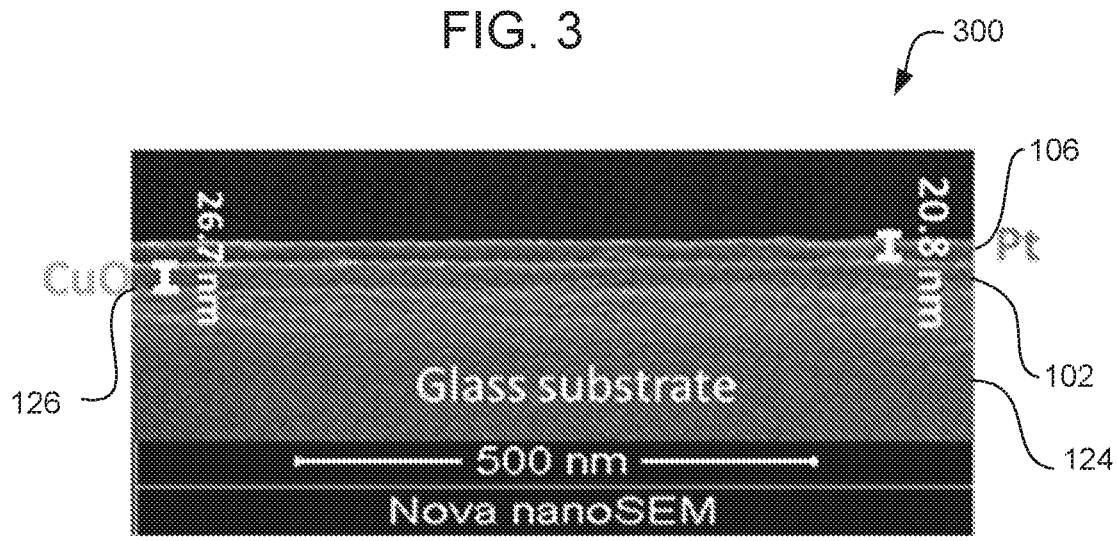
FIG. 3 is an SEM image capturing a sectioned portion of a glucose sensing device like the one shown in FIGS. 1 and 2.

FIG. 3 is an SEM image 300 showing aspects of a sensor 104, including a metal electrode 106, a thin, insulating metal oxide layer 102, and a glass substrate 124, in accordance with at least one embodiment. In production, the thin metal oxide insulating layer 102 can be produced by oxidizing a layer of the base metal by heat in the presence of an oxidizer. In some cases, a thin layer of metal, such as Cu, may be present between the metal oxide layer 102 and substrate 124 at, e.g. an interface 126 between these layers. However, in most embodiments, no additional metal layer is present.

EXAMPLES

In each of the following examples, the following sample introduction method was used. Initially, a 1V voltage bias was applied across each tested sensor by contacting the metal electrodes of each sensor with testing probes. An initial time period of about 20 s was allowed to ensure that the applied voltage was not disturbing the device state, at which time a drop of deionized water and glucose solution was placed on the device and allowed to touch the insulating metal oxide surface at a sensor gap (e.g. gap 108) as well as the adjacent electrodes (e.g. metal electrodes 106). When the drop of solution as applied, an instantaneous increase in the current across the sensor was observed, and the current was allowed to stabilize for a predetermined period of time, as shown in the following figures. Although the glucose concentrations of the drops of solution varied, the pH of each sample was approximately 7.

Figure 4:
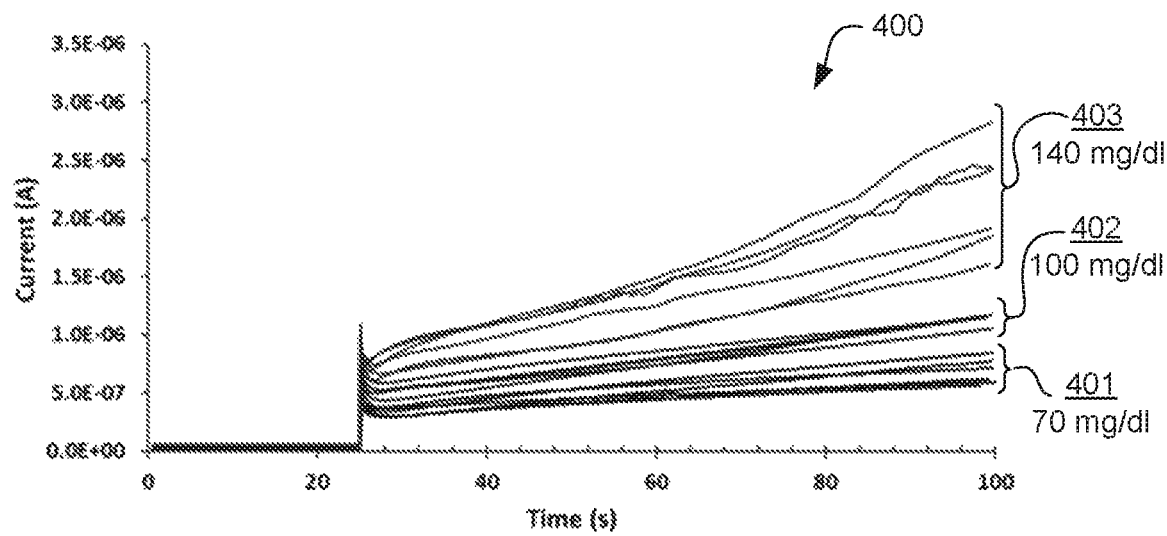
FIG. 4 is a chart showing current levels as a function of time for samples having known concentrations of blood glucose across a series of fresh sensors.

FIG. 4 is a chart 400 illustrating the measured current across a sensor, like sensors 104, over time when subjected to an applied voltage of 1V and when supplied directly with a glucose-containing sample of known glucose level. The samples were tested in sets of six duplicates, at glucose concentrations of 70 mg/dl (401), 100 mg/dl (402), and 140 mg/dl (403). These concentrations span low, medium, and high blood glucose levels for an adult human. As shown, the detected currents for each sample increase over time, but tend to cluster according to glucose concentration. The samples were each tested on fresh devices made to the same specification.

Figure 5:
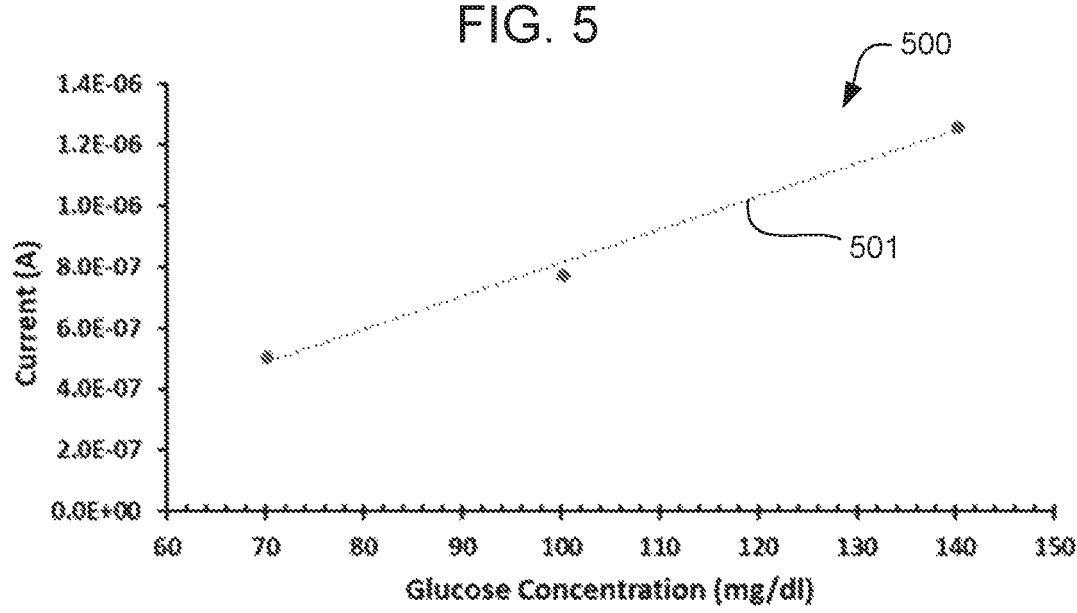
FIG. 5 is a chart showing averaged current levels at a selected time for the samples of FIG. 4.

FIG. 5 is a chart 500 illustrating average current data obtained with respect to FIG. 4 at a set time point of 60 seconds as a function of glucose concentration. A linear curve 501 can be applied to the averaged data, demonstrating that the measured current can be related directly to a glucose concentration.

Figure 6:
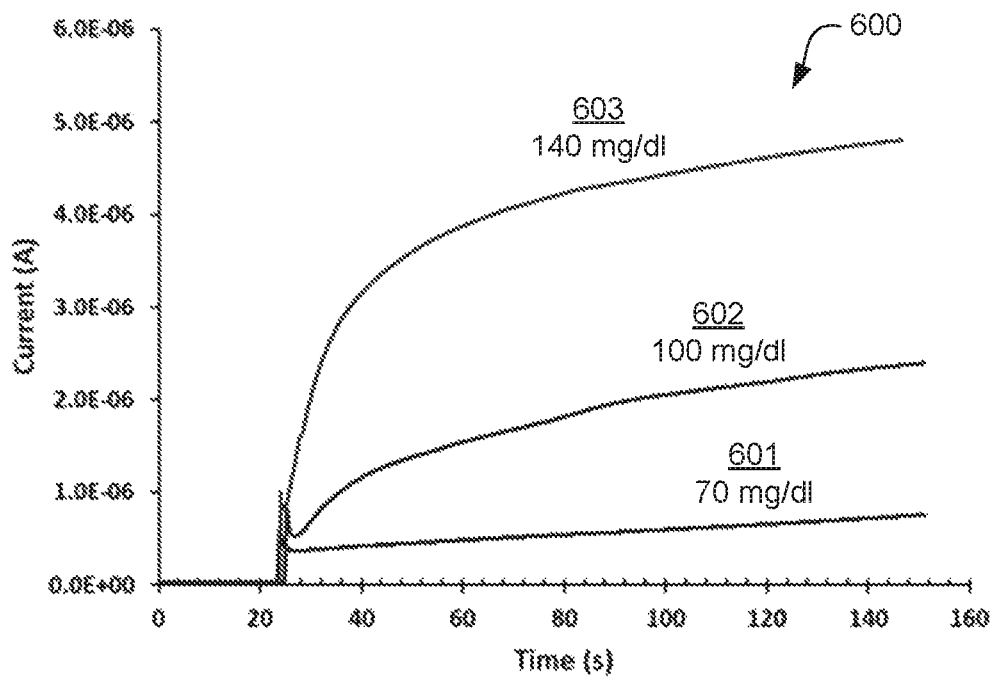
FIG. 6 is a chart showing current levels over time for samples having known concentrations of blood glucose across the same sensor, dried but without washing the sensor between samples.

FIG. 6 is a chart 600 illustrating the measured current across a sensor, like sensors 104, where each sample is subjected to testing on the same sensor. In the corresponding test method, the sensors were dried between samples, but not rinsed or washed. Samples were tested at glucose levels of 70 mg/dl (601), 100 mg/dl (602), and 140 mg/dl (603). As shown, even when re-used with minimal cleaning, the glucose sensor can obtain highly differentiable readings for different glucose levels.

Figure 7:
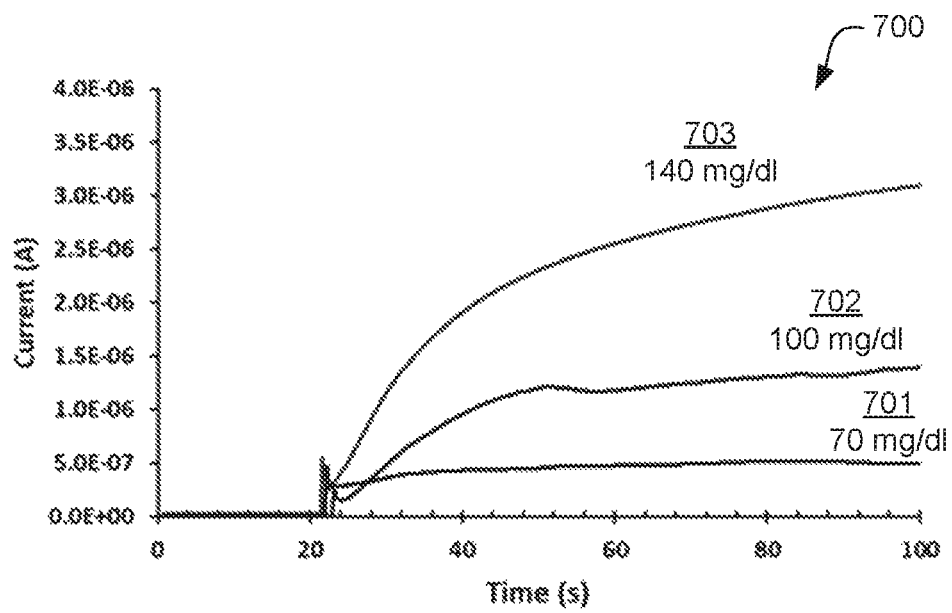
FIG. 7 is a chart showing current levels over time for samples having known concentrations of blood glucose across the same sensor, washed and dried between samples.

FIG. 7 is a chart 700 illustrating the measured current across a sensor, like sensors 104, where each sample is subjected to testing on the same sensor, but in which the sensors are both washed and dried between samples. Samples were tested at blood glucose levels of 70 mg/dl (701), 100 mg/dl (702), and 140 mg/dl (703). Although the total current associated with the curves of FIGS. 6 and 7 differ, the profiles of the data remain similar and the different glucose levels are easily differentiated.

Figure 8:
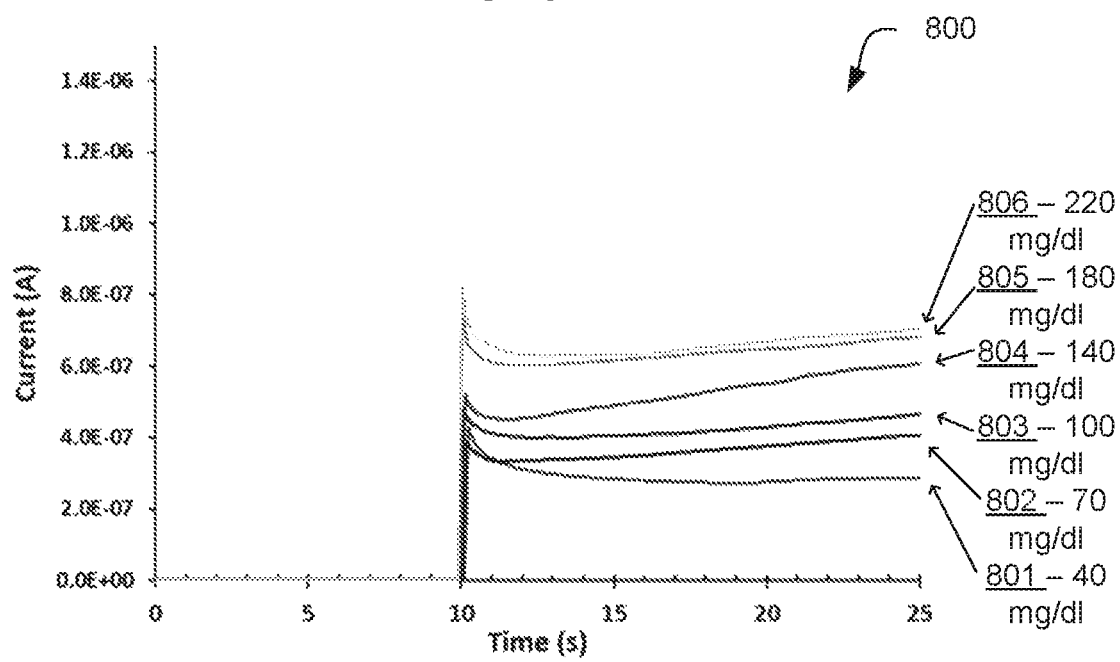
FIG. 8 is a chart showing current levels over time for a series of samples at known blood glucose levels across fresh devices from a new wafer.

FIG. 8 is a chart 800 illustrating measured currents across sensors with test samples at a wide range of glucose levels, and using fresh devices from a new wafer. As shown, samples were tested at glucose levels of 40 mg/dl (801), 70 mg/dl (802), 100 mg/dl (803), 140 mg/dl (804), 180 mg/dl (805), and 220 mg/dl (806). As shown, the currents across the sensors stabilized at readily differentiable levels and in a linear progression, suggesting that the sensors can be used to obtain repeatable glucose detection results.

Figure 9:
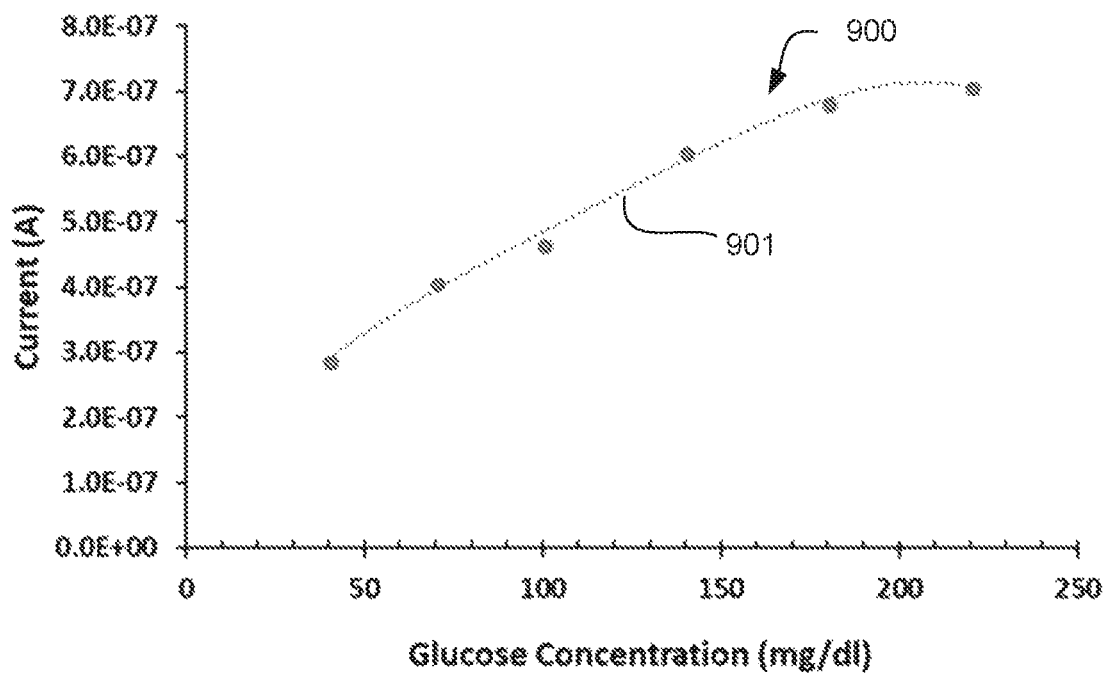
FIG. 9 is a chart showing the current levels for the samples of FIG. 8 at a selected time.

FIG. 9 is a chart 900 illustrating the current data obtained with respect to FIG. 8 at a set time point of 25 seconds and as a function of glucose concentration. A curve 901 is a close linear fit to the data, excepting the data point for the 220 mg/dl sample 806. This data point suggests that glucose levels above 180 mg/dl may saturate the glucose sensors 104, however, such glucose concentrations are already well above healthy blood glucose levels, suggesting that the device is suitable as a glucose sensor for human use.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A non-enzymatic glucose sensor, comprising:
   an insulating metal oxide layer having a flat two-dimensional top surface, wherein the metal oxide is selected from the group consisting of NiO, Cu2O, CuO, TiO2, ZnO, SnO2, MnO2, and Co3O4;
   at least one pair of metallic electrodes comprising a first metallic electrode and a second metallic electrode arranged on the flat two-dimensional top surface of the insulating metal oxide layer and separated by a gap containing the metal oxide layer; and
   a probe comprising a voltage supply and current sensor, wherein the probe is arranged to:
   provide a voltage across the first metallic electrode and the second metallic electrode to generate a current through direct interaction between glucose in a liquid sample and the flat two-dimensional top surface of the insulating metal oxide layer, and
   measure the current between the first metallic electrode and the second metallic electrode.

2. The non-enzymatic glucose sensor of claim 1, further comprising an electrically inert substrate supporting the insulating metal oxide layer.

3. The non-enzymatic glucose sensor of claim 1, wherein the at least one pair of metallic electrodes comprises a plurality of pairs of metallic electrodes, the plurality of pairs of metallic electrodes are arranged in a grid on the insulating metal oxide layer.

4. The non-enzymatic glucose sensor of claim 1, wherein the gap has a width of approximately 50 μm, and wherein the first metallic electrode and the second metallic electrode have a width of approximately 3 mm.

5. The non-enzymatic glucose sensor of claim 1, wherein the first metallic electrode and the second metallic electrode have electrode thicknesses from 10 nm to 30 nm and the insulating metal oxide layer has an oxide layer thickness from 10 nm to 30 nm.

6. The non-enzymatic glucose sensor of claim 1, wherein the voltage supply is configured to deliver the voltage of approximately 1V.

7. The non-enzymatic glucose sensor of claim 1, wherein the first metallic electrode and the second metallic electrode are Pt electrodes.

8. The non-enzymatic glucose sensor of claim 1, wherein the insulating metal oxide layer is composed of CuO.

9. The non-enzymatic glucose sensor of claim 1, wherein the non-enzymatic glucose sensor is capable of differentiating dissolved glucose levels in the liquid sample ranging from 40 mg/dl to 180 mg/dl when the liquid sample is at a pH of 7.

10. The non-enzymatic glucose sensor of claim 1, wherein the at least one pair of metallic electrodes are partially embedded in the insulating metal oxide layer.

11. The non-enzymatic glucose sensor of claim 1, further comprising: an interface layer positioned between the insulating metal oxide layer and a substrate supporting the insulating metal oxide layer.

12. A non-enzymatic glucose sensor, comprising:
an insulating metal oxide layer having a flat two-dimensional top surface, wherein the metal oxide is selected from the group consisting of NiO, Cu2O, CuO, TiO2, ZnO, SnO2, MnO2, and Co3O4;
at least one pair of metallic electrodes comprising a first metallic electrode and a second metallic electrode arranged on the flat two-dimensional top surface of the insulating metal oxide layer and separated by a gap containing the metal oxide layer;
a probe comprising a voltage supply and current sensor, wherein the probe is arranged to;
provide a voltage across the first metallic electrode and the second metallic electrode to generate a current through direct interaction between glucose in a liquid sample and the flat two-dimensional top surface of the insulating metal oxide layer, and
measure the current between the first metallic electrode and the second metallic electrode; and
an interface layer comprising a metal positioned between the insulating metal oxide layer and an electrically inert substrate supporting the insulating metal oxide layer.

13. A method of detecting blood glucose, the method comprising:
placing a blood sample on a sensor comprising a pair of first and second metallic electrodes arranged on an insulating metal oxide layer having a flat two-dimensional top surface, wherein the metal oxide is selected from the group consisting of NiO, Cu2O, CuO, TiO2, ZnO, SnO2, MnO2, and Co3O4, and separated by a gap containing the metal oxide layer;
applying a voltage between the first and second metallic electrodes to generate a current through direct interaction between glucose in the blood sample and the flat two-dimensional top surface of the insulating metal oxide layer;
measuring the current between the first and second metallic electrodes; and
determining a blood glucose level of the blood sample based on the measured current.

14. The method of claim 13, further comprising: selectively removing a subset of ions from the blood sample prior to placing the blood sample on the sensor.

15. The method of claim 13, wherein the blood sample is not diluted.

16. The method of claim 13, wherein the blood sample has a pH of approximately 7.

17. The method of claim 13, wherein the voltage is 1V.

18. The method of claim 13, further comprising:
placing the blood sample on a plurality of sensors comprising a plurality of pairs of the first and second metallic electrodes arranged on the metal oxide layer, each pair of the first and second metallic electrodes is separated by a respective plurality of gaps containing the metal oxide layer;
applying a respective voltage between the respective pair of the first and second metallic electrodes in each sensor of the plurality of sensors;
measuring a plurality of currents through the respective pairs of the first and second metallic electrodes of the plurality of sensors; and
determining the blood glucose level of the blood sample based on the plurality of measured currents.

* * * * *